United States Patent [19]

Crawford

[11] 4,368,140

[45] Jan. 11, 1983

[54] HALOGENATION PROCESS IN THE PRESENCE OF CYANOQUINONE CATALYST

[75] Inventor: Robert J. Crawford, Cincinnati, Ohio

[73] Assignee: The Procter & Gamble Company, Cincinnati, Ohio

[21] Appl. No.: 14,527

[22] Filed: Feb. 23, 1979

Related U.S. Application Data

[62] Division of Ser. No. 814,963, Jul. 12, 1977, Pat. No. 4,148,811.

[51] Int. Cl.$^3$ ................................................ C07C 1/66
[52] U.S. Cl. .............................. 252/426; 252/429 R; 252/438; 260/396 N
[58] Field of Search .................. 252/426, 429 R, 438; 260/396 N

[56] References Cited

U.S. PATENT DOCUMENTS

| | | | |
|---|---|---|---|
| 3,162,641 | 12/1964 | Acker et al. | 260/396 N |
| 3,558,671 | 1/1971 | Martin | 260/396 N |
| 3,739,008 | 6/1973 | Martin | 260/396 N |

OTHER PUBLICATIONS

R. C. Wheland & Wheland & E. L. Martin, "Synthesis of Substituted 7,7,8,8-Tetracyanoquinodimethanes", J. Org. Chem., vol. 40, No. 21, 1975, pp. 3101–3109.

*Primary Examiner*—Jacqueline V. Howard
*Attorney, Agent, or Firm*—J. J. Yetter; S. J. Goldstein; M. P. Brennan

[57] ABSTRACT

Halogenation is carried out regiospecifically in the presence of a cyanoquinone.

4 Claims, No Drawings

HALOGENATION PROCESS IN THE PRESENCE OF CYANOQUINONE CATALYST

This is a division, of application Ser. No. 814,963, filed July 12, 1977, now U.S. Pat. No. 4,148,811.

BACKGROUND OF THE INVENTION

The present invention relates to compositions and processes for halogenating carboxylic acids, acid halides and acid anhydrides at the α-carbon atom in the presence of a cyanoquinone compound.

The halogenation of organic compounds at a specific carbon atom (i.e., regiospecifically) is difficult, especially on an industrial scale. In general, halogenation reactions tend to occur to some extent at all available carbon-hydrogen linkages in the molecule undergoing halogenation.

Some regioselectivity in halogenation reactions has been achieved heretofore. For example, the treatment of aliphatic carboxylic acids having at least one α-hydrogen atom with halogens such as bromine or chlorine in the presence of a phosphorus halide catalyst comprises the well-known Hell-Volhard-Zelinsky preparation of α-halo acids. However, chlorination reactions carried out according to the HVZ procedure are not regiospecific and mixtures of chlorinated products are typically secured. For the most part, the HVZ halogenation is used to brominate carboxylic acids and is, therefore, expensive as compared with the corresponding chlorination reaction.

By the present invention, it has been discovered that cyanoquinone compounds can be used in the α-halogenation of carboxylic acids, carboxylic acid anhydrides and carboxylic acid halides. The resulting α-halogenated products are useful as lubricant additives and as intermediates for the production of lubricants, and as surfactants and surfactant intermediates.

RELATED REFERENCES

The general topic of the directive effect of the carboxyl group on the chlorination of aliphatic systems is treated by Little, Sexton, et al., *Journal of the American Chemical Society* 91 7098, (1969). See also, U.S. Pat. No. 3,584,036 to Sexton, et al., which relates to α-chlorination reactions.

Other publications relating to regiospecific halogenation reactions include: Y. Ogata, et al., *J. Org. Chem.*, 40, 2690 (1975); Y. Ogata, et al., *Tetrahedron*, 26, 5929 (1970); Y. Ogata, et al., *Nippon Kagaku Kaishi*, 1517 (1975) [*Chem. Abstr.* 83, 178 39 (1975)]; Y. Ogata, et al., Japanese Pat. No. 75-135024; Y. Ogata, et al., Japanese Patent No. 74-24913; A. F. Young, U.S. Pat. No. 3,634,504; D. N. Harpp, et al., *J. Org. Chem.*, 40, 3420 (1975); and H. Haschke, German Pat. No. 2,440,213.

While the foregoing references relate to various means for achieving the regiospecific halogenation of organic compounds, especially carboxylic acids, the present invention employs an entirely new catalyst for this purpose. This invention also provides higher yields of the desired mono-chlorinated product, and in shorter times, than do the art-disclosed processes. Moreover, the process herein is especially suitable for α-halogenating both short chain and the longer-chain fatty acids, i.e., those in the chain length range above about $C_{10}$ which are especially useful as detersive surfactants. In this regard, the present invention provides a marked improvement over the process disclosed in U.S. Pat. No. 3,584,036, cited above.

In addition to the foregoing, U.S. Pat. No. 3,988,369 to Pearson, Oct. 26, 1976, teaches a process for halogenating organic compounds in the presence of a trialkyl phosphate.

SUMMARY OF THE INVENTION

The present invention encompasses a process for halogenating carboxylic acids, acid anhydrides and acid halides (all hereinafter "carboxylate compounds") having at least one reactive alpha hydrogen substituent, comprising contacting said carboxylate compound with a halogen (especially chlorine) or halogen source in the presence of an effective amount of a cyanoquinone compound and acidic auxiliary agent, as described more fully hereinafter.

The present invention also encompasses, as a composition of matter, a mixture comprising the cyanoquinone material and the acidic auxiliary agent. The invention also encompasses, as a composition of matter, a halogenation reagent comprising a halogen (especially chlorine) or halogen source and the aforesaid mixture of cyanoquinone material and auxiliary agent. The foregoing compositions-of-matter are especially adapted for the halogenation, especially chlorination, of carboxylate compounds.

A representation of the reaction of the present process with organic acids is as follows:

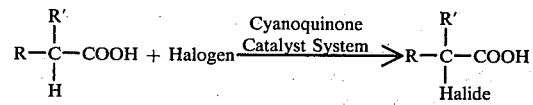

where R and R' are hydrocarbyl or hydrogen substituents, as described more fully hereinafter.

DETAILED DESCRIPTION OF THE INVENTION

The present invention encompasses a process for halogenating carboxylate compounds. The carboxylate compounds used herein are characterized by at least one reactive α-hydrogen substituent, which is displaced by a halogen atom during the process. In the practice of the invention, the carboxylic acids, acid chlorides, or carboxylic acid anhydrides are contacted with a halogen or halogen source in the presence of an effective amount of a cyanoquinone material and an acidic auxiliary agent.

By "halogenating" herein is meant displacing an α-hydrogen substituent with halogens other than fluorine. As is well known, fluorination reactions are carried out under special conditions and are therefore not contemplated in the practice of this invention. The present process is particularly useful for chlorinating or brominating carboxylate compounds and, on an industrial scale, is especially useful for chlorination reactions.

By "carboxylate compound" herein is meant carboxylic acids (and salts), carboxylic acid halides and carboxylic acid anhydrides.

By "effective amount" herein is meant an amount of the cyanoquinone material and auxiliary agent sufficient to direct the halogenation reaction regiospecifically such that it occurs almost exclusively at the α-hydrogen substituent of the carboxylate compound.

The cyanoquinone materials and acidic auxiliary agents are described in more detail hereinafter.

By "comprising" herein is meant that various other compatible materials may be present in the reaction mixtures during the halogenation reaction in such proportions as will not adversely affect the α-halogenation of the carboxylate compounds. For example, various solvents and the like can optionally be present. The term "comprising" thus encompasses and includes the more restrictive terms "consisting of" and "consisting essentially of" within its scope, so long as the processes and compositions of this invention include the specified ingredients, which are critical to the practice of the invention.

All percentages herein are on a mole basis, unless otherwise specified.

The carboxylate compounds which are α-halogenated in the manner of this invention comprise carboxylic acids and carboxylic acid-derived materials. These carboxylate compounds include the free acids and salts, the acid anhydrides and the acid halides.

The present process can be used to α-halogenate carboxylate compounds, especially carboxylic acids, comprising from about 2 to about 30 carbon atoms. (Of course, for the corresponding symmetrical carboxylic acid anhydride, equivalent compounds will comprise from about 4 to about 60 total carbon atoms.) The process herein is especially useful for α-halogenating the $C_3$ to $C_{18}$ carboxylic acids. However, for halogenating the shorter members in this class, other art-disclosed processes are adequate, albeit sub-optimal. The special economic advantages of the present process are particularly noteworthy when α-halogenating, especially α-chlorinating, the $C_6$–$C_{18}$ carboxylate materials for which the art-disclosed processes yield mixed results. Accordingly, the present process is especially useful for α-halogenating, especially α-chlorinating, carboxylate materials based on lauric acid, myristic acid, palmitic acid, stearic acid, and mixtures thereof.

The process of this invention is not limited with regard to the halogenation agent. Elemental halogens, liquid or gaseous, can be used. Chlorine gas is especially convenient, economical and preferred for use herein. Bromine can also be used, but is more expensive, as is iodine. Halogen sources other than elemental halogens can also be used. Such alternate halogen sources include, for example, well-known organic halogenating agents such as N-chlorosuccinimide (NCS) and N-bromosuccinimide (NBS).

Cyanoquinones

The cyanoquinone materials used herein are all members of the well-known class of compounds which have recently been the subject of intensive study as electrically-conductive organic solids. Reviews of these materials, methods of preparation and a list of references to additional compounds and preparative methods appear in the articles by Wheland and Gillson, *Journal of the American Chemical Society*, 98, 3916 (1976) and Wheland and Martin, *J. Org. Chem.*, 40, 3101 (1975), incorporated herein by reference.

In general, the cyanoquinones useful herein are characterized by the moiety:

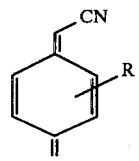

where R can be H or one or more substituent groups, e.g., halogen, alkoxy, alkyl, thioalkyl, CN, etc. See Wheland and Martin, above.

The tetracyanoquinodimethane (TCNQ) compounds preferred for use herein are of the formula (R as above):

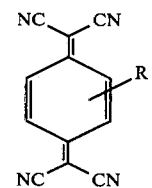

Other, specific examples of cyanoquinones useful herein include hexacyanobutadiene (HCBD) and tetracyanonaphthoquinodimethane (TNAP), represented by the following formulas

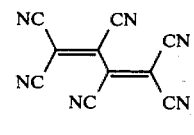

HCBD

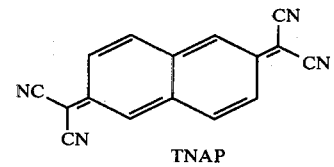

TNAP

TCNQ, TNAP and HCBD are prepared by techniques known in the literature. (While HCBD is not, in the most formal sense, a quinone structure, its extended conjugated system of electrons is "quinone-like." Accordingly, HCBD is considered a cyanoquinone in the present invention.)

Auxiliary Agents

The auxiliary agents used in the practice of this invention include many of the common acidic materials known in the art for use in halogenation reactions. Such acidic materials include both Lewis acids and inorganic protonic acids which are of considerably greater acid strength than hydrocarbyl carboxylic acids. Typical examples of such acidic auxiliary agents include acetyl chloride, $PBr_3$, $PCl_3$, thionyl chloride, sulfuryl chloride, oxalyl chloride, sulfonyl chloride, $PCl_5$, phosgene, fluorosulfonic acid, chlorosulfonic acid, and trifluoromethanesulfonic acid. The most highly preferred auxiliary agent herein is chlorosulfonic acid.

It is to be understood that carboxylic acid halides (especially acid chlorides) are operative in the practice of this invention as auxiliary agents when α-halogenating carboxylic acids or anhydrides thereof. However, carboxylic acid halides can themselves be halogenated if they contain an α-hydrogen substituent. The α-halogenation of carboxylic acid halides is carried out in the presence of a more acidic auxiliary agent such as ClSO$_3$H, PCl$_3$, etc., and the cyanoquinone material. This is not a preferred halogenation method, inasmuch as it requires the separate preparation of a stoichiometric amount of acid chloride, which is thereafter α-halogenated.

The most preferred catalyst system herein comprises a mixture of TCNQ and chlorosulfonic acid. Various ratios of these materials can be employed, but a ca. 1:5–1:50 mole ratio of TCNQ:ClSO$_3$H is convenient.

The most preferred halogenation reagent herein comprises gaseous chlorine and the aforesaid mixture of TCNQ and chlorosulfonic acid. Of course, the chlorine in this reagent is replenished as it is exhausted during the reaction. Replenishment of the chlorine is most conveniently carried out by bubbling gaseous chlorine into the reaction mixture.

The halogenation reaction of this invention is carried out by contacting the carboxylate compound with the halogen or halogen source in the presence of a cyanoquinone material and acidic auxiliary agent at a temperature of about 70° C., or greater. Chlorination reactions using elemental chlorine as the halogen are carried out at temperatures above about 130° C., preferably at temperatures within the range from about 150° C. to about 250° C. When halogen sources such as the N-halosuccinimides are used, temperatures of about 70° C.–250° C. are operative and convenient. Bromination and iodination reactions are carried out under similar temperature conditions.

The process herein can be carried out in the presence or absence of inert solvents. Preferably, the reaction is carried out without the use of solvents, and this is both convenient and economical on a commercial scale. Indeed, the use of solvents can lead to undesirable side-reactions involving halogenation of many of the common hydrocarbon solvents. Under the reaction temperatures specified hereinabove, the carboxylate compounds are liquids and are quite convenient to use in that state without additional solvents.

Typical use concentrations of the cyanoquinones relative to the carboxylate compounds are 0.01–10.0 mole percent, preferably 0.05–5.0 mole percent, most preferably 0.05–0.5 mole percent.

Typical use concentrations of the acidic auxiliary agents relative to the carboxylate compounds are 0.1–10 mole percent, preferably 1–5 mole percent.

The following examples illustrate the practice of this invention but are not intended to be limiting thereof. Percentage yields are in parentheses.

EXAMPLE I

Preparation of 2-Chlorostearic Acid

A 1-liter five-neck round bottom flask is placed in an efficient fume hood and is fitted with a mechanical stirrer, thermometer, Dry Ice condenser, and two fritted gas dispersion tubes (opposite necks). The two dispersion tubes are connected via PVC tubing to a T-connector, the third arm of which is connected to a chlorine gas source containing an in-line flowmeter capable of reading 200–1000 ml/min.

The dispersion tubes are removed temporarily, and the flask is charged with 569.0 g (2.0 moles) of powdered stearic acid. The stearic acid is melted by warming the flask with a heating mantle while stirring at low speed. When the acid has melted (temperature approximately 80° C.), 1.65 g (0.008 mole) of TCNQ (Aldrich Chemical Co.) is added. The chlorine gas flow to the dispersion tubes is started and set at a rate of 250 ml/min. Chlorosulfonic acid, 4.0 ml (0.063 mole) is pipetted rapidly into the flask (temp. <90° C.) and the dispersion tubes are immediately fitted to the flask so that the chlorine is evolved well beneath the surface of the liquid. The stirrer is adjusted to a high speed setting, and the solution is heated as rapidly as possible to 150° C. (Immediately prior to the addition of chlorosulfonic acid, full line voltage is applied to the heating mantle. When the solution temperature reaches 130° C., the voltage is cut to 0, allowing the temperature to coast to 150° C.) During the heating period, the Dry Ice condenser is filled with a Dry Ice-alcohol slurry. When the temperature reaches 148° C., the chlorine flow rate is increased to 1000 ml/min. This point is considered time 0 for purposes of timing the reaction.

Throughout the reaction, the solution temperature is maintained at 150°±3° C. by careful adjustment of the current to the heating mantle. Since the reaction is mildly exothermic, this temperature is usually maintained during the first half hour with no current applied to the mantle. During the second half hour, the cooling effect of condensing chlorine necessitates constant monitoring of the solution temperature and mantle setting. At 65 minutes reaction time, the chlorine flow rate is reduced to 250 ml/min. At 75 min., the heating mantle is removed and is replaced by an ice bath, and the dispersion tubes and condenser are removed. When the solution temperature reaches 80°–90° C., the entire reaction mixture is poured into 1500 ml of acetonitrile. The resulting mixture is warmed on a steam bath until a clear, yellow, homogeneous solution is obtained. The solution is placed in an ice bath and stirred or swirled vigorously to effect crystallization of the product. After standing at 0° C. overnight, the product is collected by suction filtration, washed thoroughly with cold acetonitrile, and vacuum dried to afford 535.5 g (84%) of 2-chlorostearic acid, M.P. 63.5°–64° C.

As an optional modification of the foregoing procedure, an additional 0.8 g portion of TCNQ can be added at 50 min. reaction time. This serves to prevent the formation of minor by-products that result if the reaction is allowed to run beyond the time when starting material is consumed. With this modification, the yield of recrystallized 2-chlorostearic acid is increased to 89%.

The process of Example I is carried out with lauric acid, myristic acid, palmitic acid, and commercial tallow fatty acids, i.e., mixtures of lauric, myristic, palmitic and stearic acids, respectively. High yields (ca. 90%) of the α-chlorinated acids are secured in each instance.

The process of Example I is carried out using the following acidic auxiliary agents in place of the chlorosulfonic acid: PBr$_3$; PCl$_3$; PCl$_5$; acetyl chloride, thionyl chloride; sulfuryl chloride; oxalyl chloride; sulfonyl chloride; phosgene; fluorosulfonic acid; chlorosulfonic acid; stearoyl chloride; and trifluoromethane sulfonic acid. In each instance, excellent yields of pure 2-chlorostearic acid are secured.

The process of Example I is carried out using HCBD and TNAP, respectively, as the cyanoquinone agent (0.008 moles). In each instance, good yields of the desired 2-chlorostearic acid are secured.

The process of Example I is repeated using acetic, propionic, butyric, pelargonic, pentadecanoic, margaric, arachidic, behenic, tricosanoic, and cerotic acids, respectively, and their respective anhydrides, and the α-chlorinated products are secured.

EXAMPLE II

α-Halogenation of Acid Halides and Anhydrides

Following the procedure of Example I, stearoyl chloride is reacted with chlorine in the presence of ClSO$_3$H and TCNQ. The product is distilled to provide substantially pure 2-chlorostearoyl chloride.

The foregoing reaction is repeated using stearic anhydride and the α-chlorinated anhydride is secured.

In a modification of the process of Example II, the chlorine gas is replaced by liquid bromine and the corresponding α-brominated compound is secured.

EXAMPLE III

Mixtures especially adapted for use in the α-halogenation of carboxylate compounds are as follows:

| Mixture Number | Cyanoquinone (moles) | Auxiliary Agent (moles) |
|---|---|---|
| 1 | TCNQ 1 | ClSO$_3$H 1 |
| 2 | TCNQ 1 | ClSO$_3$H 10 |
| 3 | TCNQ 10 | ClSO$_3$H 1 |
| 4 | TCNQ 1 | CF$_3$SO$_3$H 10 |
| 5 | TCNQ 1 | PCl$_5$ 20 |
| 6 | TCNQ 1 | PCl$_3$ 10 |
| 7 | TCNQ 10 | FSO$_3$H 1 |
| 8 | TCNQ 1 | CH$_3$COCl 1 |
| 9 | TCNQ 1 | SO$_2$Cl$_2$ 2 |
| 10 | TNAP 1 | ClSO$_3$H 10 |
| 11 | HCBD 1 | ClSO$_3$H 10 |
| 12 | TNAP 1 | CF$_3$SO$_3$H 20 |
| 13 | HCBD 1 | PCl$_5$ 5 |
| 14 | TNAP 1 | PBr$_3$ 10 |
| 15 | TNAP 5 | POCl$_3$ 2 |
| 16 | HCBD 2 | SO$_2$Cl$_2$ 1 |
| 17 | HCBD 5 | PCl$_3$ 1 |
| 18 | HCBD 10 | FSO$_3$H 1 |
| 19 | TNAP 1 | CF$_3$SO$_3$H 1 |
| 20 | HCBD 1 | FSO$_3$H 1 |

The foregoing mixtures are typically used at concentrations of 0.01%–10% of the carboxylate compound being halogenated and the reaction proceeds substantially exclusively at the α-CH group.

EXAMPLE IV

The process of the present invention can be carried out using free halogens in the manner described hereinbefore. Organic halogenating agents such as N-chlorosuccinimide can also be employed, as follows.

In a 50 ml 3-neck round bottom flask fitted with a condenser, thermometer, and magnetic stirrer were placed 11.4 g (0.04 mole) stearic acid, 8.0 g (0.06 mole) N-chlorosuccinimide, 0.1 ml (0.0015 mole) chlorosulfonic acid, and 0.04 g (0.0002 mole) TCNQ. The flask was placed in a heating bath set at 150° C. The mixture was stirred during heating, and a homogeneous liquid phase was formed. The solution temperature continued to rise above that of the heating bath, and a sudden exothermic reaction occurred in which the reaction temperature increased to ca. 220° C. The reaction mixture was cooled and dissolved in chloroform, and the resulting solution was washed thoroughly with dilute aqueous sodium chloride solution. After drying and removal of the chloroform, the residue was recrystallized from acetonitrile to afford 8.9 g (70%) of 2-chlorostearic acid which was equivalent in purity to the product of Example I.

EXAMPLE V

Following the procedures of Examples I and II herein, carboxylate compounds are α-chlorinated, α-brominated and α-iodinated in the presence of the following mixtures of substituted TCNQ and acidic auxiliary agents:

| Mixture Number | Substituted Cyanoquinone* (moles) | Auxiliary Agent (moles) |
|---|---|---|
| 1 | 1 TCNQ (OMe) | 10 ClSO$_3$H |
| 2 | 2 TCNQ (OMe)$_2$ | 5 ClSO$_3$H |
| 3 | 3 TCNQ (OMe) (OEt) | 10 FSO$_3$H |
| 4 | 10 TCNQ (OEt) (SMe) | 3 CF$_3$SO$_3$H |
| 5 | 1 TCNQCl | 1 PCl$_5$ |
| 6 | 5 TCNQBr | 1 PBr$_3$ |
| 7 | 1 TCNQClMe | 10 SO$_2$Cl$_2$ |
| 8 | 1 TCNQBrMe | 10 POCl$_3$ |
| 9 | 1 TCNQIMe | 15 PBr$_3$ |
| 10 | 1 TCNQCl$_2$ | 10 CH$_3$COCl |
| 11 | 2 TCNQBr$_2$ | 5 SO$_2$Cl$_2$ |
| 12 | 1 TCNQI$_2$ | 10 PCl$_3$ |
| 13 | 3 TCNQ (i-Pr)$_2$ | 20 ClSO$_3$H |

*Prepared as described in Wheland and Martin, above.

The foregoing mixtures are typically used at concentrations of 0.01%–10.0% of the carboxylate compound being halogenated and the reaction proceeds substantially exclusively at the α-CH group to provide the α-halogenated carboxylate compound.

As can be seen from the foregoing, the present process provides an improved means for carrying out α-halogenations, especially α-chlorinations, of carboxylate compounds, especially carboxylic acids. By the present invention, the use of cyanoquinone materials substantially improves yields of α-chlorinated products and greatly decreases side-reactions which have heretofore led to undesirable by-product formation. TCNQ, HCBD, TNAP and derivatives thereof are available by art-disclosed processes for use in the present invention.

What is claimed is:

1. A catalyst system, comprising: a cyanoquinone material selected from tetracyanoquinodimethane and derivatives thereof, and an acidic auxiliary agent selected from PCl$_3$, PCl$_5$, PBr$_3$, thionyl chloride, sulfuryl chloride, oxalyl chloride, sulfonyl chloride, acetyl chloride, phosgene, fluorosulfonic acid, chlorosulfonic acid, and trifluoromethane sulfonic acid.

2. A catalyst system according to claim 1 wherein the mole ratio of the tetracyanoquinodimethane or tetracyanoquinodimethane derivative to the auxiliary agent is in the range of 1:5 to 1:50.

3. A catalyst system according to claim 2 consisting essentially of tetracyanoquinodimethane and ClSO$_3$H.

4. A catalyst system, comprising: a cyanoquinone material and an acidic, auxiliary agent selected from the group consisting of PCl$_3$, PCl$_5$, PBr$_3$, thionyl chloride, sulfuryl chloride, oxalyl chloride, sulfonyl chloride, acetyl chloride, phosgene, fluorosulfonic acid, chlorosulfonic acid, and trifluoromethane sulfonic acid.

* * * * *